(12) United States Patent
Castor

(10) Patent No.: US 12,337,039 B2
(45) Date of Patent: Jun. 24, 2025

(54) ROOM TEMPERATURE STABLE, SINGLE SHOT MRNA VACCINE FOR COVID-19

(71) Applicant: Trevor Percival Castor, Arlington, MA (US)

(72) Inventor: Trevor Percival Castor, Arlington, MA (US)

(*) Notice: Subject to any disclaimer, the term of this patent is extended or adjusted under 35 U.S.C. 154(b) by 494 days.

(21) Appl. No.: 17/699,359

(22) Filed: Mar. 21, 2022

(65) Prior Publication Data

US 2022/0296728 A1  Sep. 22, 2022

Related U.S. Application Data

(60) Provisional application No. 63/163,920, filed on Mar. 21, 2021.

(51) Int. Cl.
| | |
|---|---|
| *A61K 47/69* | (2017.01) |
| *A61K 9/51* | (2006.01) |
| *A61K 47/34* | (2017.01) |
| *A61P 31/14* | (2006.01) |
| *A61K 39/00* | (2006.01) |

(52) U.S. Cl.
CPC ........ *A61K 47/6937* (2017.08); *A61K 9/5153* (2013.01); *A61K 9/5192* (2013.01); *A61K 47/34* (2013.01); *A61P 31/14* (2018.01); *A61K 2039/55555* (2013.01)

(58) Field of Classification Search
CPC .. A61K 47/6937; A61K 9/5153; A61K 39/12; A61K 2039/55555; A61P 31/14; C12N 2770/20034
See application file for complete search history.

(56) References Cited

PUBLICATIONS

Tenchov et al, Lipid Nanoparticles From Liposomes to mRNA Vaccine Delivery, A Landscape of Research Diversity and Advancement, ACS Nano, 15, 11, 16982-17015. (Year: 2021).*

* cited by examiner

*Primary Examiner* — Carlos A Azpuru

(57) ABSTRACT

This disclosed technology relates to a new mRNA COVID-19 vaccine that is stable at room temperature, requires only one injection, and is less prone to patient hypersensitivity reactions. The vaccine is practical to deploy globally during vaccination campaigns for current and future coronavirus pandemics and other infectious diseases. The disclosed technology is a method and system for producing the vaccine, and also a double-encapsulated mRNA vaccine product. The method uses double nanoencapsulation of an mRNA vaccine, first in phospholipid nanosomes and then in biodegradable polymer nanospheres. The method may be carried out as a continuous flow, integral, or two-stage processes. The method and system use supercritical fluid technology for nanoencapsulating mRNA in a solvent free process that minimizes loss of potency and preserves antigenicity of the nanoencapsulated mRNA and eliminates residual organic solvents in the final product. The double-encapsulated mRNA vaccine product is stable at room temperature and can be administered in a single shot to humans.

7 Claims, 3 Drawing Sheets

ROOM TEMPERATURE STABLE, SINGLE SHOT MRNA VACCINE FOR COVID-19

GOVERNMENT SUPPORT

Embodiments of the present invention were conceived without Federal sponsorship or finding.

FIELD OF THE INVENTION

This invention relates to a COVID-19 mRNA vaccine that is stable at room temperature, requires only one injection, thus being more practical to deploy nationally and globally during vaccination campaigns, and is less prone to cause hypersensitivity reactions. The invention also relates to a method and system for producing the vaccine.

BACKGROUND OF THE INVENTION

COVID-19 has quickly become the most impactful healthcare, social, and economic crisis of our lifetime. The pandemic has disrupted everyday life abruptly and unpredictably at a global scale. The impact is even more pronounced for racial and economic minorities and for socioeconomically disfavored individuals and groups. To assist in the resolution of these crises, the present invention is for a single-shot, room-temperature stable mRNA vaccine for COVID-19. This vaccine, in addition, can be easily modified to cover mutant viruses that constantly emerge, and provides be a significant component of the vaccination armamentarium during the current and future pandemics.

COVID-19, the multiorgan disease caused by the novel coronavirus SARS-CoV-2, has become the most impactful healthcare, social, and economic crisis of our lifetime. SARS-CoV-2 is genetically related to the previous two coronaviruses that caused human outbreaks in the $21^{st}$ century, SARS-CoV and MERS-CoV. Even though COVID-19 mortality is lower than the one associated with the other two coronavirus diseases, the pandemic has impacted, by mid-March 2022, >470 million people worldwide, and caused >6 million deaths. Had the COVID-19 mortality been closer to those of SARS and MERS, the impact of the current pandemic would be incomparably more catastrophic.

The COVID-19 pandemic has impacted global healthcare, social life, and national economies in ways that most people have not experienced in their lifetime and has been compared with the 1918-1919 influenza pandemic that is also known as "the mother of all pandemics." In parallel, the poverty gap in the US and worldwide has become more accentuated. The impact is even more accentuated for racial and economic minorities and for socioeconomically disfavored individuals and groups.

Early during the pandemic, social distancing and face covering have emerged as the main preventative strategies, and the only ones consistently shown to reduce transmission. It is unanimously accepted that only a safe and effective vaccine will provide a path to return society to pre-pandemic life.

From >100 vaccine leads pursued since early 2020, as of mid-March 2022, several vaccines have been deployed in the US and the rest of the world. The Pfizer-BioNTech mRNA vaccine appears to be very effective, but vaccination is hindered by the −70° C. storage condition that this vaccine requires. This challenge becomes even more acute considering that vaccination will require at least two annual doses and boosters. An additional challenge associated with this vaccine is the threat of hypersensitivity reactions, possibly caused by polyethylene glycol (PEG) that is included in the formulation. The Moderna vaccine, also mRNA-based, requires storage at −20° C. The need for cold storage, the requirement of booster doses, and the potential for adverse allergic reactions, are major drawbacks of both these vaccines.

SUMMARY OF THE INVENTION

The only realistic solution to end the pandemic appears to require the availability of safe and efficacious vaccines. To address these shortcomings, the present technology is for a COVID-19 mRNA vaccine that is stable at room temperature, requires only one injection, thus being more practical to deploy nationally and globally during vaccination campaigns, and is less prone to cause hypersensitivity reactions.

As discussed above, a large number of vaccine leads were pursued in 2020, and only four emerged as most promising ones. The Pfizer-BioNTech mRNA vaccine, approved in the US in mid-December 2020, appears to be very effective, but vaccination is hindered by the −70° C. storage condition that this vaccine requires, in this vaccine requires at least 2 doses and boosters. The Moderna vaccine, another mRNA vaccine, also requires two injections and boosters, and storage at −20° C. Due to the relatively short-lived persistence of antibodies to coronavirus, which was estimated to be in the range of a few months, and the possibility that the virus will become endemic, we envision that COVID-19 vaccination will become a recurring and critical necessity to ensure that healthcare, education, social life, and economies can function uninterrupted.

Vaccines developed by Johnson & Johnson and Astra Zeneca-Oxford University are based on an adeno virus delivery enable construct that can be stored at refrigerator temperatures of 2-10° C. The most promising of these vaccines appear to be the mRNA constructs for reasons of non-viral vector mode of delivery, clinical efficacy and large-scale manufacturability. The major drawback of these vaccines appears to be cold storage and the requirement of booster doses.

The shortcomings of prior approaches to a vaccine are overcome by the present disclosed technology. The disclosed method and system are a two-stage encapsulation process.

The first stage nanoencapsulates mRNA in phospholipid nanosomes (small, uniform liposomes) to facilitate cellular uptake. In the first nanoencapsulation stage, raw phospholipid materials are solubilized by SuperFluids [SFS] at a specific pressure and temperature (e.g., 3,000 psig and 40° C.) in a high-pressure circulation (HPC) loop. The lipid-enriched SFS exits the HPC loop and is mixed with a solution of mRNA in an in-line mixer. The mixture is then continuously decompressed into a biocompatible solution in a decompression chamber at a temperature of 4° C. and pressures just below the critical pressure (Pc) of the SFS, around 1,000 psig. As a result of pressure reduction and concomitant reduction in density, phospholipids come out of solution as lipid fragments that thermodynamically coalesce into vesicles nanoencapsulating mRNA. The released SFS is vented or recycled into the feed side of the process after cleaning and sterilization.

In the second stage of the double nanoencapsulation process, the phospholipid nanosomes are re-pressurized and become the feed for a second nanoencapsulation apparatus. This stream is mixed with a SFS stream enriched with a biodegradable polymer such as PLGA solubilized in an SFS at a specific pressure and temperature (e.g., 2,500 psig and 30° C.). The mixture is then decompressed continuously to atmospheric pressure (zero psig) at 4° C. The separated SFS is vented and the recovered product, mRNA double nanoencapsulated in phospholipid and biodegradable polymer, is recovered and lyophilized.

Proprietary Critical Fluid Nanosomes (CFN™) technology is used to nanoencapsulate the mRNA molecule that encodes the coronavirus Spike protein in phospholipid nanosomes and then into biodegradable polymer nanospheres using modifications of our proprietary Polymer Nanospheres Technology (PNS) to sustain mRNA release. The antigenicity and integrity of the nanoencapsulated mRNA are characterized before and after nanoencapsulation and coating to determine the best process conditions that ensure stability at room temperature after lyophilization.

The capability to release mRNA over time will allow vaccination with a single intramuscular injection and will mark a milestone in coronavirus vaccination strategies. The vaccine does not contain polyethylene glycol (PEG), which was historically linked to hypersensitivity reactions and is suspected to be responsible for some of the adverse allergic effects that were seen after administration of the Pfizer vaccine.

DETAILED DESCRIPTION

Figure 1:
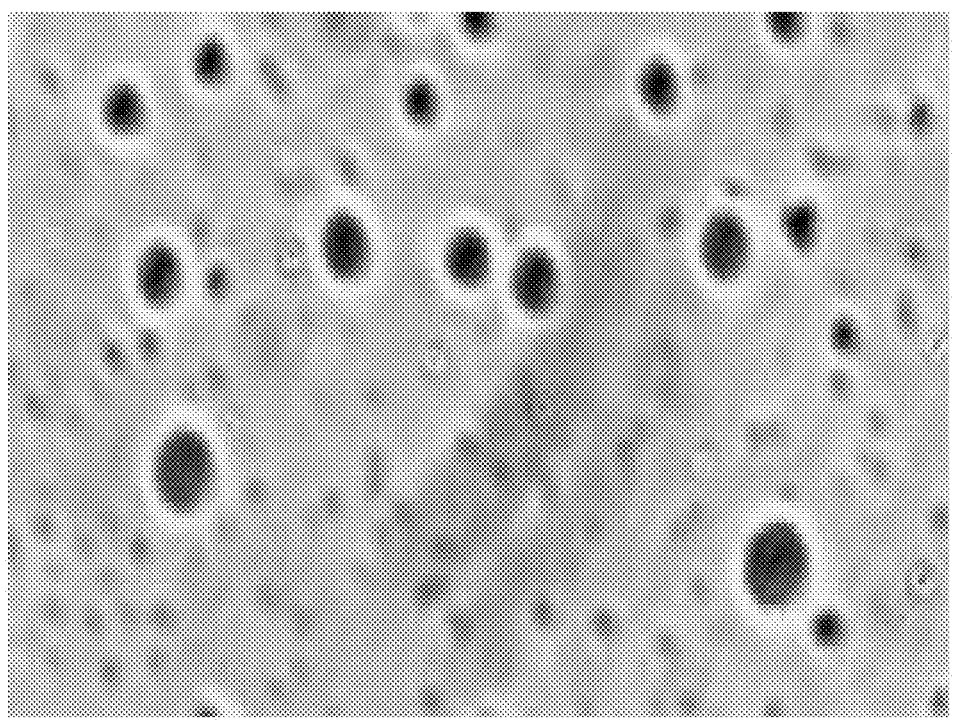
FIG. 1 shows is a photomicrograph showing rPA-02 Nanospheres.

It is intended that the subject matter contained in the following description be interpreted in an illustrative rather than a limiting sense.

COVID-19, the multiorgan disease caused by the novel coronavirus SARS-CoV-2, previously 2019-nCoV, has become the most impactful healthcare, social, and economic crisis of our lifetime. SARS-CoV-2 is genetically related to the SARS-CoV (~10% fatality rate) and MERS-CoV (~37% fatality rate). Even though COVID-19 mortality is lower than the one associated with the other two coronavirus diseases, the pandemic has impacted, in the first year, >470 million people worldwide. Had the COVID-19 mortality been closer to those of SARS and MERS, the impact of the current pandemic would be incomparably more catastrophic.

Social distancing and face masks have emerged as the main preventative strategies, and the only ones consistently shown to reduce transmission. Besides supportive measures, the only therapeutic option for COVID-19 patients developed early in the pandemic was Remdesivir (Gilead Biosciences), which was available in the US only for compassionate use, and antibodies from convalescent plasma, which was not deployed on a commercial scale.

Most of the vaccines developed to date have multiple shortcomings as discussed. To address these this shortcoming, the disclosed technology generates a COVID-19 mRNA vaccine that is a single-shot vaccine, that is stable at room temperature and more practical to deploy nationally and globally during campaigns and, additionally, less prone to cause hypersensitivity reactions.

Using our proprietary Critical Fluid Nanosomes (CFN™) technology, we first nanoencapsulate mRNA molecules that encode the coronavirus Spike protein gene in phospholipid nanosomes. We then nanoencapsulate these nanosomes into biodegradable polymer nanospheres using modifications of our proprietary Polymer Nanospheres Technology (PNS) to sustain mRNA release and confer room temperature stability of lipids and nanoencapsulated mRNA. We establish operating parameters and conditions for the continuous encapsulation of the mRNA into phospholipid nanosomes and coating with biodegradable polymers. If needed, we also establish operating parameters and conditions for lyophilization and reconstitution of the polymer-coated phospholipid nanosomes. We characterize infectivity, antigenicity, and integrity of the nanoencapsulated mRNA before and after nanoencapsulation and coating to determine the best process conditions and product.

Stabilities of these nanoformulations are evaluated at different temperatures with readouts of infectivity, antigenicity and integrity. Extended release of the mRNA into a biological system is also investigated. These analyses are performed before and after reconstituting the vaccine from lyophilized nanoparticles and select the best nanoformulations for in vivo testing.

The safety, pharmacokinetics, and immunogenicity of the nanoencapsulated antigen are evaluated and challenge studies in two animal models are performed, in anticipation of subsequent clinical studies.

Our invention lies in the double nanoencapsulation of an mRNA vaccine construct in lipid nanospheres and biodegradable polymers. We also innovate in the use of continuous flow, solvent-free, single-step processes. The impact of this development to produce room temperature stable mRNA vaccines would be significant to US and worldwide vaccination for the current and future coronavirus pandemics and other infectious diseases.

Based on these studies, the best nanoformulation for scale-up is selected for more detailed in vitro and in vivo characterization, to establish potency and release specifications, and conduct regulatory studies.

To overcome the problems with prior COVID-19 vaccines, the disclosed technology is a novel process using SuperFluids™ for making biodegradable polymer nanospheres that do not require organic solvents. SuperFluids™ are supercritical, critical or near-critical fluids with or without polar cosolvents (aka SFS). SFS used are typically gases which, when compressed, exhibit enhanced thermodynamic properties of solvation, selection, penetration, and expansion. We have explored these properties on a cellular level to improve molecular interactions, mass transfer rates, reduce interfacial tensions and shorten processing times.

The use of SFS greatly reduces processing time and costs associated with preparation of biodegradable polymer microspheres containing vaccine products while maintaining the uniformity and integrity of the nanoparticles. Such 'green' technology-based fluids will replace the use of toxic organic solvents. In Aphios' SuperFluids™ polymer nanospheres [SFS-PNS]process, a biodegradable polymer is dissolved in SuperFluids™ and decompressed through a nozzle into an aqueous solution containing the target therapeutic. Alternatively, the polymer-rich SuperFluids™ stream is mixed a solution of the biodegradable polymer in ethanol, acetone or suitable solvent in an inline mixer before decompression in a suitable aqueous buffer. The resulting decompression creates polymer nanospheres which simultaneously encapsulates the lipid-encapsulated vaccine. The safety of this approach has been validated by the use of supercritical fluids as microbicidal and virucidal technologies. PNS has been utilized to nanoencapsulate Bryostatin-1, to make it orally bioavailable as an Alzheimer' disease therapeutic. PNS has been used in targeting several enzymes, proteins, and peptides e.g., biosynthetic insulin, to make it orally bioavailable in a rat model of diabetes. Nanoencapsulated vaccine antigens such as recombinant protein antigen (rPa) using PNS have been made for use in anthrax vaccinations (FIG. 1).

mRNA is first nanoencapsulated in phospholipid nanosomes (small, uniform liposomes) to facilitate cellular uptake. In the first nanoencapsulation stage, raw phospholipid materials are solubilized by SFS at a specific pressure and temperature (e.g., 3,000 psig and 40° C.) in the high-pressure circulation (HPC) loop shown in the upper left half of FIG. 2. The lipid-enriched SFS exits the HPC loop and is mixed with a solution of mRNA in an in-line mixer. The mixture is then continuously decompressed into a biocompatible solution in a decompression chamber at a temperature of 4° C. and pressures just below the critical pressure (Pc) of the SFS, around 1,000 psig. As a result of pressure reduction and concomitant reduction in density, phospholipids come out of solution as lipid fragments that thermodynamically coalesce into vesicles nanoencapsulating mRNA. The released SFS is vented or recycled into feed side of the process after cleaning and sterilization.

Figure 2:
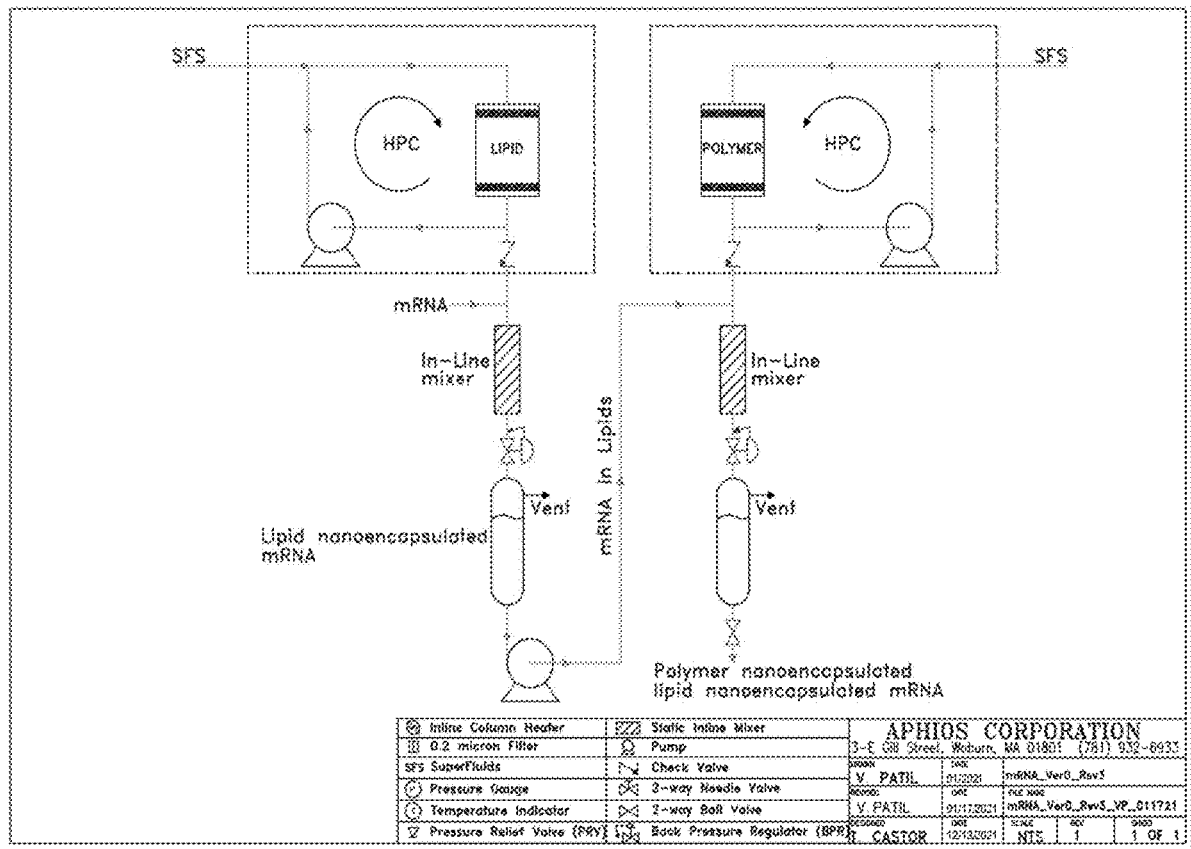
FIG. 2 is a schematic diagram showing the process flow for Continuous Flow Double Nanoencapsulation of mRNA in Phospholipid Nanosomes and Polymer Nanospheres.

In the second stage of the double nanoencapsulation process, the phospholipid nanosomes are re-pressurized and become the feed for the apparatus shown in FIG. 2 (right). This stream is mixed with a SFS stream enriched with a biodegradable polymer such as PLGA solubilized in an SFS at a specific pressure and temperature (e.g., 2,500 psig and 30° C.). The mixture is then decompressed continuously to atmospheric pressure (zero psig) at 4° C. The separated SFS is vented and the recovered product, mRNA double nanoencapsulated in phospholipid and biodegradable polymer, is recovered and lyophilized.

Figure 3:
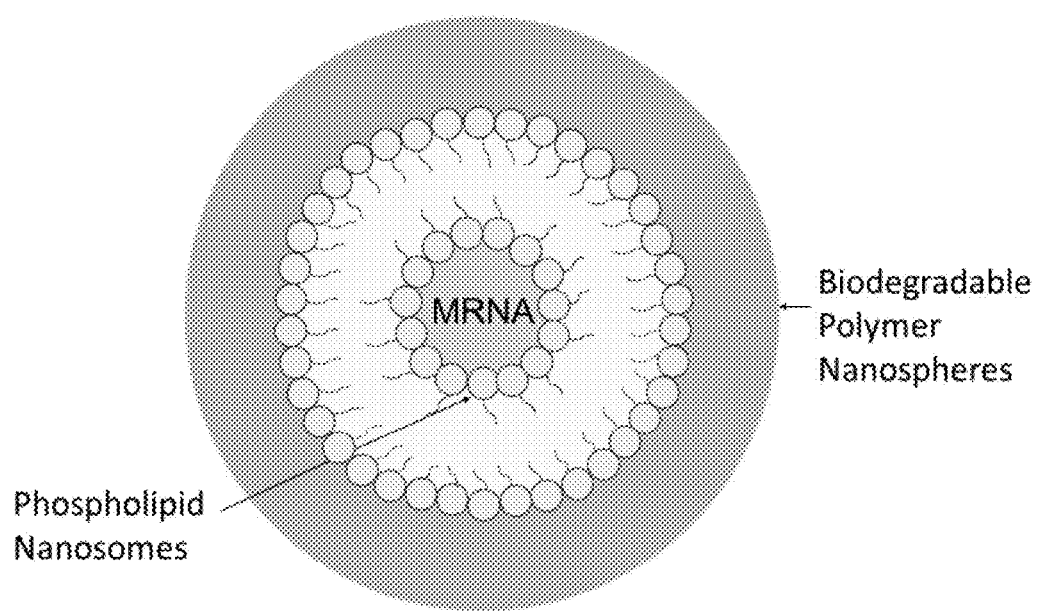
FIG. 3 is an illustration of double nanoencapsulated mRNA.

There are several levels of strategic innovation and invention in our approach to develop a single-shot, sustained release room temperature stable mRNA COVID-19 vaccine. The key innovation is the double nanoencapsulation of mRNA, first in phospholipid nanosomes and then in biodegradable polymer nanospheres. The second level of innovation is the sustained mRNA release, which impactfully changes the vaccine paradigm from a two-dose to a single-shot vaccine. Additionally, the absence of PEGylation promises a better safety profile of this vaccine. A third level of innovation is the continuous process of double encapsulation in a single step process. A fourth level of innovation is the use of a solvent-free process, using SuperFluids™, that minimizes loss of potency and preserves antigenicity of the nanoencapsulated mRNA and eliminates the presence of residual organic solvents in the finished product (FIG. 3).

Encapsulation of mRNA in Phospholipid Nanosomes

In the CFN™ process, supercritical, critical or near-critical fluids with or without polar cosolvents [SuperFluids™ (SFS)] at appropriate conditions of pressure and temperature are utilized to solvate phospholipids, cholesterol and other nanosomal raw materials. After a specific residence time in the high-pressure circulation loop at a specific temperature and pressure shown in FIG. 2, the phospholipid-rich SFS stream is mixed with a solution of mRNA in a specific compositional ratio in an in-line mixture. The resulting mixture is decompressed via a backpressure regulator (valve) though a dip tube with a nozzle into a decompression chamber that contains phosphate-buffered saline or other biocompatible solution. Bubbles will form at the injection nozzle tip because of SFS depressurization and phase-conversion into a gas, and the solvated phospholipids will deposit out at the phase boundary of the aqueous bubble. As the bubbles detach from the nozzle into the aqueous solution, they rupture, causing bilayers of phospholipids to peel off, thereby encapsulating mRNA and spontaneously sealing themselves to form phospholipid nanosomes. Product volatilization and oxidation as well as processing time and organic solvent usage are significantly reduced with the use of SuperFluids™ that preserves the integrity of both the phospholipid materials and the mRNA active. The temperature of the equipment downstream of the HPC is maintained at a lower temperature than the HPC in order to protect the mRNA from thermal degradation, e.g., the lipid nanoencapsulated mRNA will be maintained at 4° C.

SuperFluids™ and Phospholipid Raw Materials

Different SFSs such as $CO_2$, near-critical propane, or an alternative fluorocarbon solvent are utilized. Based on prior experience, we use SFS propane and 20% ethanol at 3,000 psig and 40° C. The near-critical propane has a dipole moment of 0.084 Debyes, and thus exhibits a much higher solvation power for phospholipids. Propane is considered GRAS (generally regarded as safe) by the FDA when used under GMP conditions in the food and pharmaceutical industries. Lipid materials are selected on the basis of previous studies and further optimized based on their solubility in the SuperFluids™ under appropriate operational conditions.

Synthetic lipid, DPPC (1,2-dipalmitoyl-sn-glycero-3-phosphocholine) from Lipoid GmbH of Germany is selected for the nanoencapsulation experiments. A synthetic lipid is chosen because it is uniform in-chain length and saturation of bonds. The molar ratio of total lipid to drug will range from ~5:1 to ~20:1.

Nanosomes Procedure

The mRNA is encapsulated in phospholipid nanosomes in the apparatus shown in FIG. 2. We produce different nanosomes by various lipid materials in the range of 100 to 200 (±50) nm.

Encapsulation of Lipid Nanoencapsulated mRNA in Polymer Nanospheres

While highly promising, hydrophobic microspheres still present several technical formulation challenges in creating a clinically acceptable product. Conventional microsphere manufacture involves organic solvents, such as methylene chloride and ethyl acetate, which pose concerns about toxicity from residual traces of solvent in the final product. Large-scale production of polymeric microspheres utilizing these processing steps and large quantities of organic solvents is time-consuming, costly, and inefficient. In addition, any exposure of the therapeutic agent to the organic solvent can adversely affect the integrity of the final product from residual organics that can adversely affect drug stability and negatively impact patients' health and/or increase regulatory requirement burdens.

We overcome these limitations by using SuperFluids™ [SFS] to replace the usage of toxic organic solvents. In the SFS polymer nanospheres process, shown schematically on the right side of FIG. 2, a biodegradable polymer is first dissolved in SuperFluids™ in a high-pressure circulation loop at a specific pressure and temperature. After a specific residence time in the HPC, the polymer-rich SFS stream is mixed with a solution of mRNA in phospholipid nanosomes in a specific compositional ratio in an in-line mixture and decompressed through a nozzle into an aqueous solution; as a result of decompression, polymer nanospheres are formed encapsulating the lipid nanoencapsulated mRNA. Alternatively, the mixture can be decompressed into liquid nitrogen or an empty vessel (spray dryer). In addition to reduction or elimination of organic solvent use, use of supercritical fluids for nanospheres imparts the advantage of immediate product sterility based on several reports (including ours) demonstrating the microbicidal and virucidal effects of supercritical fluids.

Hydroohobic Biodegradable Polymers

The technology uses pharmaceutical-grade PLGA [poly (D, L-lactide-co-glycoside) 50:50] polymer (Resomer® RG-502, Boehringer Ingelheim KG), PCL [Polycaprolactone] purchased from Sigma Aldrich and Eudragit L100 also purchased from Sigma. Specifications are presented in Table 1. To predict the solubility of these polymers in different types of SuperFluids™, Hildebrand solubility parameters are calculated using a group contribution method. The solubility parameters of PLGA and PCL are computed to be 23.82 $MPa^{0.5}$ and 20.87 $MPa^{0.5}$, respectively.

TABLE 1

Specifications of Biodegradable Polymers Used in the SFS-PNS Process

| Polymer | Chemical Formula | Polymer Composition | Molecular Weight (grams/mole) | Glass Transition Range (° C.) |
|---|---|---|---|---|
| PCL | $(C_6H_{10}O_2)_n$ | Polycaprolactone | 14,000 | −60 |
| Eudragit L100 | $(C_4H_4O_2)_n(C_4H_6O_2)_n$ | Poly(methacrylic acid-co-methacrylate) 1:1 | 125,000 | >150 |
| PLGA | $(C_3H_4O_2)_n(C_2H_2O_2)_m$ | Poly(D,L-lactide-co-glycolide) 50:50 | 7,000-17,000 | 40-55 |

Nanoencapsulation of Lipid Encapsulated mRNA

In this process, a biodegradable polymer such as PLGA is placed in the solids chamber in FIG. 2 and circulated for 30 minutes to saturate the SFS with polymer in CO2:Ethanol:: 80:20 at 2,500 psig and 30° C. The polymer-enriched SFS in the isobaric chamber is then contacted with a feed stream containing mRNA that are continuously decompressed through a nozzle into an aqueous buffer (e.g., 10% sucrose at pH 7 containing 0.1% PVA (polyvinyl alcohol)). As a result of decompression, the hydrophobic molecules come out of the SFS solution, thermodynamically self-assemble in an aqueous environment and polymer nanospheres are formed encapsulating lipid encapsulated mRNA.

Smaller and more tightly packed nanospheres exhibit significantly longer residence times in biological environments and show enhanced immunogenicity. Several operational conditions including temperature, nozzle size, and rate of decompression, that strongly influence nanospheres size and distributions have been identified. Consequently, we focus on evaluating the effects of other important parameters that affect size and distribution such as polymer type, nanospheres composition, and mRNA:polymer ratios, and how these affect stabilities in a biological environment. To do this, nanospheres of different sizes ranging from 100 to 250 (±50) nm are produced by various polymer materials and, if needed, sterilized by 0.22 μm filtration and lyophilized.

Nanospheres

Nanospheres produced are characterized in terms of their size/morphology, antigen loading efficiency, and particle integrity. In vitro release studies of the inactivated mRNA antigen from polymer nanospheres are then be carried out. Brief descriptions of the characterization procedures are as follows:

Particle Size Distributions/Morphology

A Coulter Model N4MD submicron particle size analyzer is used for measuring average particle size, size frequency distribution, and standard deviation of particle size. The morphology of the selected particles is also inspected by scanning electron microscopy (SEM) after coating the samples with gold-palladium to a thickness of 200-500 Å.

Encapsulation Efficiency

The loading efficiency of SARS-CoV-2 mRNA (such as Spike mRNA) in nanospheres is determined by dissolving a known amount of nanospheres in a 90% acetonitrile aqueous solution or another suitable solubilizing agent. The amount of the specific SARS-CoV-2 mRNA (such as Spike mRNA) is determined by Northern Blot analyses. The loading efficiency is calculated based on weight percent and optimized for immunization.

If the continuous flow double encapsulation proves difficult operationally to achieve the targeted results in a reproducible fashion (3 back-to-back) experiments, the nanoencapsulations can be performed in two separate steps.

Double nanoencapsulated mRNA formulations are formed in the size range of 100-200 nm with >90% encapsulation efficiency.

Stabilities of Nanoformulations and Sustained Release

Stabilities of these nanoformulations are evaluated at different temperatures with readouts of infectivity, antigenicity, and integrity. Extended release of the mRNA into a biological system is also investigated. These analyses are performed before and after reconstituting the vaccine from lyophilized nanoparticles to select the best nanoformulations for in vivo testing. Aliquots of nanoparticle formulations are lyophilized by placing them in glass vials connected to a vacuum chamber, vacuum pump and refrigeration unit.

Stability Studies

Stability protocols are developed per ICH (International Committee on Harmonization) guidelines which are similar to the FDA guidelines. Stability studies are conducted on different formulations in the presence of a nitrogen or argon head to displace 02. Studies are conducted on between 8 to 12 nanoformulations for further evaluation and development.

Stability studies are carried out in environmental test chambers (Percival Model I-30NL Stability Chamber (APH-EQ-12011) and VWR-Shel Labs Model 9005 Humidity Chamber (APH-EQ-11232)). Sufficient samples are tested for stability to meet the ICH stability protocol requirements for up to three years of testing. Standard (real time over 3 years) stability studies are conducted on samples that have passed the accelerated stability studies. The standard studies include 12 time points: t=0, 3, 6, 9, 12, 18, 24 and 36 months at 25° C./60% Relative Humidity (RH). In case of time constraints, accelerated stability studies are primarily utilized to evaluate the impact of temperature, humidity and time on the on stabilities of different nanoformulations. These studies are conducted at 40° C./75% RH with time point-equivalent to 1, 2 and 3 months. During this time period, stability studies will also be performed on the nanoformulations at −80° C., −20° C. and 4° C. The impact of light (NLT 1000-foot candles) and oxygen (5% and 20%) are also evaluated. The stability of the nanosomes in human plasma is tested by spiking human plasma with nanospheres and testing mRNA recovery at different intervals up to 2 days following incubation at 37° C. The following tests are performed: (i) particle size and distribution; (ii) mRNA content; and (iii) mRNA potency. SDS-PAGE is performed to determine the integrity of the viral mRNA. Northern Blotting is used to probe for the specific SARS-CoV-2 mRNAs used for encapsulation. Statistical analysis of the data sets is performed using SYSTAT®.

In Vitro Sustained Release Studies

In vitro release kinetics of the biodegradable polymer nanospheres are carried out by placing nanospheres in PBS buffer (pH=7.4) and human sera at 25° C. and 37° C. At intervals of minutes, hours, days, weeks and months, samples are taken, and the composition of the SARS-CoV-2 mRNA and polymer are quantified. Measuring the amount of SARS-CoV-2 mRNA in the supernatant to the total SARS-CoV-2 mRNA in the nanospheres allows determination of cumulative mRNA released as a function of time. The predominant mRNA that is nanoencapsulated is the mRNA encoding the viral Spike (S) protein, as this is the dominant protein responsible for viral infectivity and against which neutralizing antibody response is mounted. These parameters are compared across freshly prepared nanospheres and reconstituted nanospheres.

For cases of rapid release, PLGA ratios will be adjusted and, alternatively, PCL or Eudragit L100 will be used. Release rates will also be adjusted by either increasing the polymer:drug ratio and/or reducing the drug loading.

Based on these in vitro studies, formulations are selected based on the following specifications: (1) polymer:drug ratio of 10:1 to 5:1 or better; (2) stability (>95% retention of mRNA) under standard conditions of 25° C./60% RH; (3) unimodal particle size between 200 and 300 nm; and (4) in vitro controlled release over a 30-day period.

Safety, Pharmacokinetics, Immunogenicity and Efficacy of Nanoencapsulated mRNA

Safety, pharmacokinetics and immunogenicity of the nanoencapsulated antigen and challenge studies in two animal models are performed in anticipation of subsequent clinical studies. In vivo studies are performed using C57BL/6 mice for toxicity and biodistribution, and in the C57BL/6 transgenic derivative K18-hACE2 (Jackson Laboratories) for efficacy studies. We chose the hACE2 mouse model because its infection with SARS-CoV-2 recapitulates several features of severe COVID19 disease in humans. Infected mice show a peak on SARS-CoV-2 viremia in lungs on days 2-4, followed by inflammatory responses that lead to pulmonary dysfunction and eventually death by day 7. The dose ranges for these studies are determined by the results of in vitro studies. The vaccines are administered at weekly intervals by the intramuscular route in both studies.

Toxicity and Biodistribution Studies

For the safety study, groups of 8 C57BL/6 mice (4 male+4 female) are injected with 4 different doses of the vaccine along with a vehicle control for 8 weeks at weekly intervals for each set. The doses are none, low, medium and high, with the actual amounts determined based on in vitro results. The animals are monitored for body weight and clinical symptoms during this period. At the end of 8 weeks, animals are sacrificed and necropsied for organ damage. Histopathology is performed for the following organs: blood, spleen, brain, heart, kidney, lung, pancreas, uterus, ovaries/testes, esophagus, bladder, trachea, thymus, gut, stomach and lymph nodes. Biodistribution in these organs is determined by ELISA. Sera are prepared from the mouse blood and evaluated for the presence of antibodies against different viral proteins and by neutralization assays.

Efficacy Studies

Groups of 12 hACE2 mice (6 male+6 female) are injected with 4 levels of the vaccine. Animals are dosed by the intramuscular route and bled weekly for the measurement of antibodies to the S-protein by ELISA and neutralization antibody response against the whole virus. One to two weeks following the dose, 8 mice from each group are infected intranasally with $10^5$ $TCID_{50}$ units of SARS-CoV-2 as in previous studies, and 4 mice will be mock infected. On day 3 after infection, when maximal viral loads are reached in lungs, mice are euthanized and lungs collected for quantification of viral loads by RT-qPCR, HP and IHC analyses.

Power and Statistical Analyses

A standard deviation of 10-15% within the absolute response, an alpha level of 0.05, and a power of 0.90, an n=12 animals within each study group is obtained to achieve significance. Data are analyzed using a Student's two-tailed t-test or one-way analysis of variance (1-way ANOVA) for measured (parametric) data or a Mann-Whitney U test (M-W) or Kruskal-Wallis (K-W) test for scored (non-parametric) data. ANOVA/K-W analyses are performed along with an appropriate multiple comparison post-hoc analysis (e.g., Dunnett's/Dunn's). ANOVA/K-W tests are calculated using Prism v 8.0.2 software (GraphPad). Data analyses include potential differences between male and female mice. Significance for all tests is set at $p \leq 0.05$.

If the humoral and cellular immune responses are not satisfactory, the composition of the polymer nanospheres is modified to improve antigen release.

Humoral and cellular responses greater than 90% of the dual dose Moderna and/or Pfizer control vaccines are achieved at room or refrigerator temperature.

While this invention has been particularly shown and described with references to specific embodiments, it will be understood by those skilled in the art that various changes in form and details may be made therein without departing from the spirit and scope of the invention as defined by the appended claims.

What is claimed is:

1. A method for making double-encapsulated nanoparticles for use in vaccines that do not contain PEG or polyethylene glycol for the treatment of COVID-19—and other viral diseases, said nanoparticles having an aqueous core loaded with mRNA, a surrounding phospholipid layer, and an outer surface of biodegradable polymer enveloping the nanoparticle, the method comprising:

a) A first stage, comprising the steps of providing a source of phospholipid material in supercritical, critical or near critical fluid (SFS), providing a source of mRNA, forming a mixture of the phospholipid fluid and mRNA in an inline mixer, decompressing the mixture into a biocompatible solution in a decompression chamber wherein phospholipid lipid fragments nanoencapsulate the mRNA forming phospholipid nanosomes, and recovering the phospholipid nanosomes; and b) A second stage, comprising the steps of re-pressurizing the phospholipid nanosomes, mixing the phospholipid nanosomes with an SFS stream enriched with a biodegradable polymer, decompressing the mixture to atmospheric pressure to encapsulate the phospholipid nanosomes in the biodegradable polymer to form mRNA nanoparticles, and recovering the mRNA nanoparticles, double-encapsulated in phospholipids and a biodegradable polymer.

2. The method of claim 1, wherein the double-encapsulated mRNA is lyophilized.

3. The method of claim 1 wherein the biodegradable polymer is PLGA [poly (D, L-lactide-co-glycoside) 50:50].

4. The method of claim 1, wherein the mixing of the phospholipid and mRNA solution is followed by decompressing the mixture using a back-pressure regulator, and injecting said mixture as a stream through an injection nozzle into a decompression chamber containing an aqueous solution, wherein bubbles form at an injection nozzle, detach from the nozzle, and rupture, causing bilayers of phospholipids to peel off, encapsulating solute mRNA molecules and spontaneously sealing to form a nanoparticle having a aqueous core containing mRNA surrounded by a phospholipid layer.

5. The method of claim 1 wherein the nanoparticles prevent hypersensitivity reactions in patients.

6. The method of claim 1, wherein the method is performed as a continuous flow two-stage process for producing double-encapsulated nanoparticles in large quantities.

7. The method of claim 1, wherein the double-encapsulated nanoparticles containing mRNA induce an antigen-specific immune response to a COVOD-19 virus and other viruses in a human subject.

* * * * *